United States Patent [19]

Cianci

[11] 4,149,539

[45] Apr. 17, 1979

[54] HEMOSTATIC DEVICE

[75] Inventor: James P. Cianci, Cary, Ill.

[73] Assignee: The Kendall Company, Boston, Mass.

[21] Appl. No.: 821,452

[22] Filed: Aug. 3, 1977

[51] Int. Cl.² ............................................. A61M 25/00
[52] U.S. Cl. ............................. 128/325; 128/349 B;
  128/DIG. 26; 116/DIG. 34; 128/350 R
[58] Field of Search .............. 128/325, 343, 344, 348,
  128/349 B, 349 BV, 350, 351, DIG. 26;
  116/DIG. 8, DIG. 9, DIG. 34

[56] References Cited

U.S. PATENT DOCUMENTS

| | | | |
|---|---|---|---|
| 3,046,988 | 7/1962 | Moreau et al. | 128/325 |
| 3,730,187 | 5/1973 | Reynolds | 128/DIG. 26 X |
| 3,834,380 | 9/1974 | Boyd | 128/DIG. 26 X |
| 3,977,408 | 8/1976 | MacKew | 128/DIG. 26 X |
| 4,083,369 | 4/1978 | Sinnreich | 128/344 X |

*Primary Examiner*—Henry J. Recla
*Attorney, Agent, or Firm*—Powell L. Sprunger

[57] ABSTRACT

A hemostatic device comprising, a catheter having an elongated elastic shaft, an inflatable balloon adjacent a distal end of the shaft, and a sidearm adjacent a proximal end of the catheter. The device has a traction member comprising a retaining portion to receive the catheter shaft and sidearm, with the retaining portion being connected to an object to maintain the catheter shaft under selected tension.

15 Claims, 13 Drawing Figures

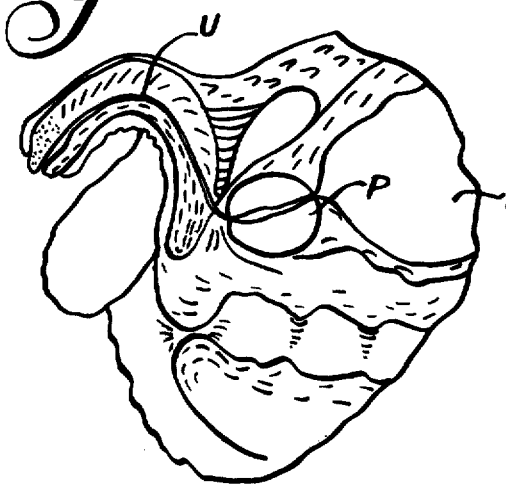
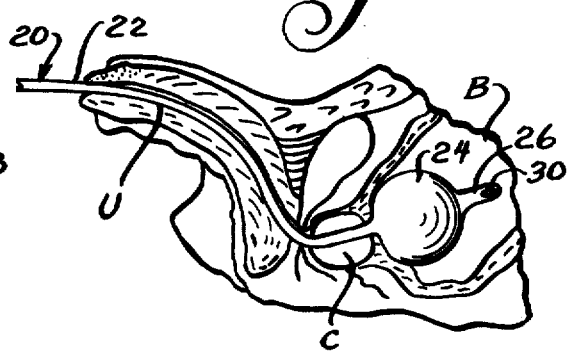
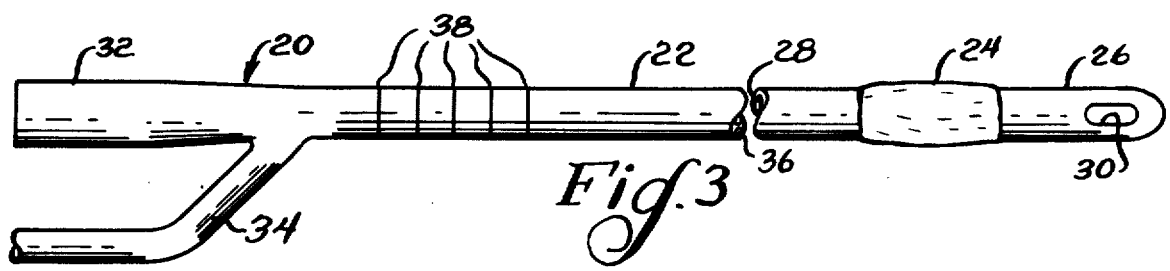
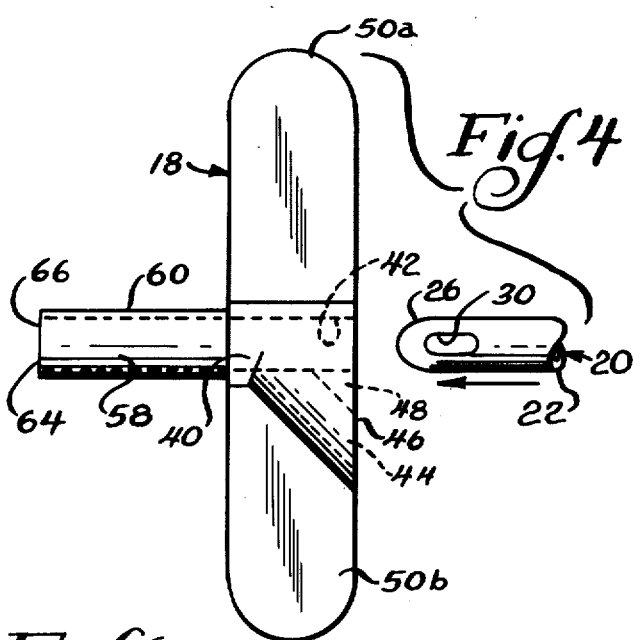
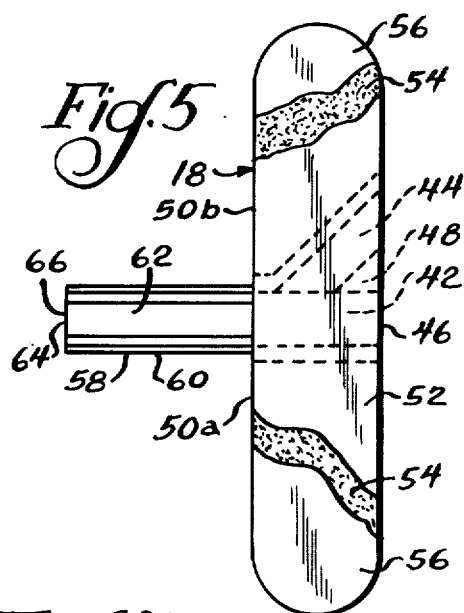
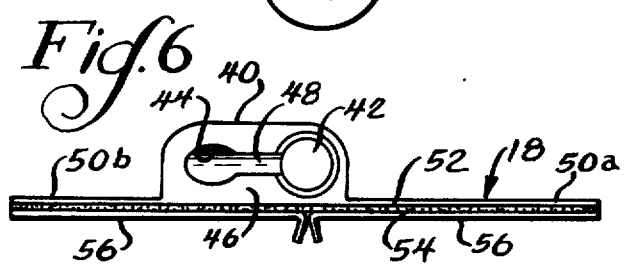
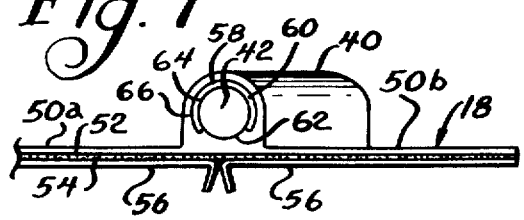

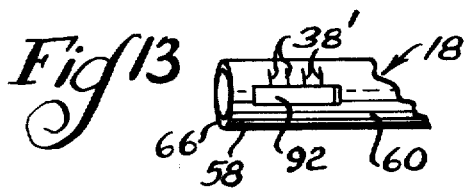
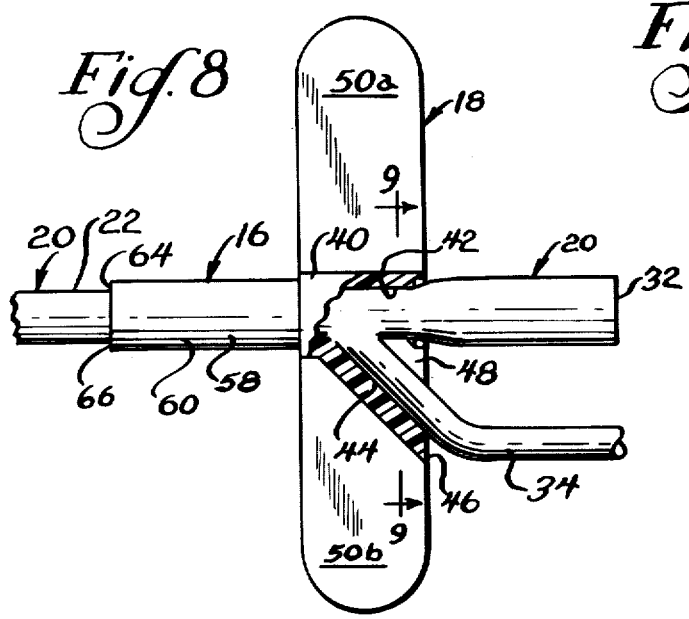
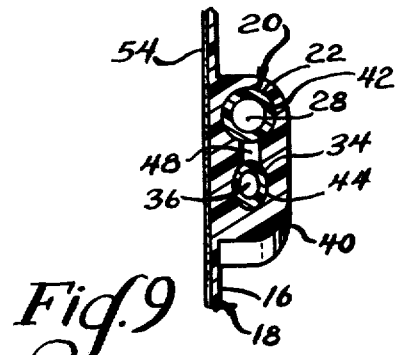
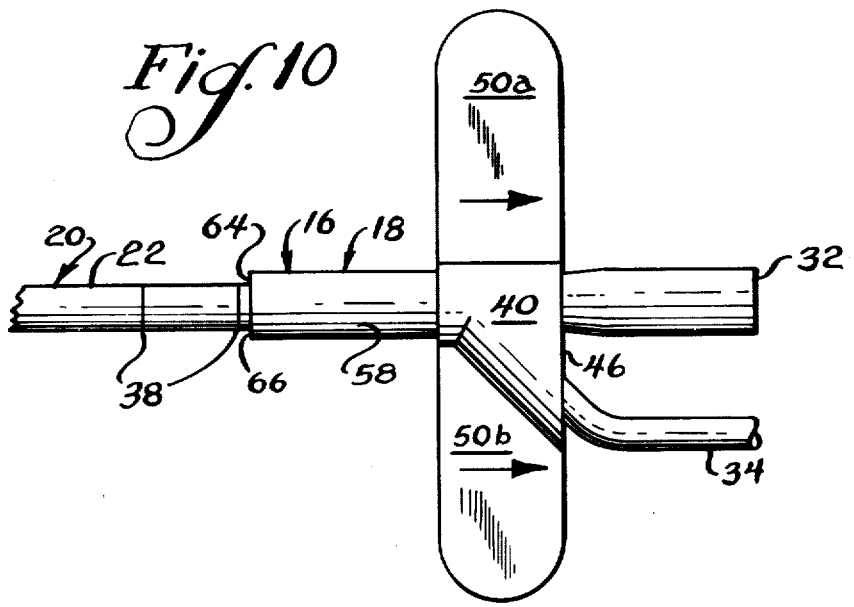

HEMOSTATIC DEVICE

CROSS-REFERENCE TO RELATED APPLICATION

This application is related to application Ser. No. 791,668, filed Apr. 28, 1977.

BACKGROUND OF THE INVENTION

The present invention relates to catheters, and more particularly to hemostatic devices.

In certain male patients it may be necessary to remove the prostate in the event that it becomes fibroid or cancerous. Generally, the prostate is removed either through a suprapubic procedure or a transurethral dissection during which a resectoscope is utilized to carve out the prostate. After the prostate has been removed, the resectoscope is withdrawn from the patient leaving a bleeding cavity or prostatic fossa adjacent the bladder where the prostate was formerly located.

In the past, the urologists have stopped the bleeding over a period of time in the following manner. A catheter having a balloon adjacent a distal end of the catheter shaft is passed through the urethra until the balloon is located in the bladder and a proximal end of the catheter is located outside the patient. The removed prostate is weighed to estimate the size of the prostatic fossa in the particular patient, and a quantity of fluid proportional to the prostatic weight is pumped into the catheter balloon in order to inflate the balloon in the bladder a sufficient amount to later prevent the balloon from falling into the prostatic fossa. Next, force is applied against the catheter shaft such that the balloon in turn applies pressure against the apex of the incised blood vessels, with the pressure being maintained for a period of time which may vary from five minutes to twenty four hours depending upon the preference of the particular urologist. The amount of force applied to the catheter by pulling its proximal end also varies with the urologist, but is believed equivalent to the force caused by a weight in the range of from 1-12 lbs. if such weight was attached to the proximal end of the catheter.

In this manner the bleeding is eventually stopped, although the procedure is accompanied by a great amount of uncertainty. Initially, the urologist does not have any clear indication from experience concerning the amount of force which is desired to stop bleeding, and even if known, the urologist could not determine whether the desired amount of force is being applied to accomplish hemostasis unless actual weights are attached to the proximal end of the catheter shaft. In this regard, it is necessary to apply sufficient force against the catheter to obtain hemostasis, yet undue pressure by the inflated balloon against the blood vessels in the bladder may result in pressure necrosis and must be prevented.

Thus, it is desirable to provide the urologist with a convenient indication of the applied forces and pressures, in order that he can determine through experience the proper range of forces required for hemostasis while preventing pressure necrosis in the bladder. Once such range has been ascertained, it is desirable that the urologist may readily determine whether the proper amount of force is being applied against the catheter during a particular procedure without the inconvenience of hanging weights from the catheter.

The hemostatic catheters disclosed in said application Ser. No. 791,668 solve the above problem and accomplish the desired results. In addition, it would be desirable to facilitate attachment of the catheter proximal end to the patient or other object in order to maintain the catheter shaft under selected tension.

SUMMARY OF THE INVENTION

A principal feature of the present invention is the provision of an improved hemostatic device.

The device of the present invention comprises, a catheter having an elongated elastic shaft, an inflatable balloon adjacent a distal end of the shaft, and a sidearm adjacent the proximal end of the catheter extending outwardly from the shaft. The device has a traction member comprising, a retaining portion having a bore, and a side channel communicating with the bore and extending at an angle from the bore toward a proximal end of the retaining portion. The retaining portion has a slot extending between the channel and bore, and the traction member has means for connecting the retaining portion to an object.

A feature of the present invention is that the catheter may be placed in the retaining portion of the traction member by inserting the catheter shaft into the retaining portion bore, and passing the catheter sidearm through the retaining portion slot to position the catheter sidearm in the retaining portion side channel.

Thus, a feature of the present invention is that the catheter may be readily positioned in the traction member preparatory to use of the hemostatic device.

Another feature of the invention is that the retaining portion firmly grips the catheter, such that the catheter shaft may be placed under tension by applying forces against the traction member.

Still another feature of the invention is that the connecting means may be attached to the patient's leg or other object to maintain the catheter shaft under selected continuous tension for accomplishing hemostasis after prostatectomy.

A further feature of the invention is that the traction member may include an indicating element for use in determining a desired amount of tension in the catheter shaft.

Further features will become more fully apparent in the following description of the embodiments of this invention and from the appended claims.

DESCRIPTION OF THE DRAWINGS

In the drawings:

FIG. 1 is a fragmentary diagrammatic view of a patient's body;

FIG. 2 is a fragmentary diagrammatic view of a patient's body illustrating a hemostatic catheter positioned to accomplish hemostasis in the prostatic fossa after prostatectomy;

FIG. 3 is a fragmentary elevational view of a hemostatic catheter;

FIG. 4 is a front plan view of a traction member for the hemostatic device of the present invention;

FIG. 5 is a back plan view, partly broken away, of the traction member of FIG. 4;

FIGS. 6 and 7 are opposed end views of the traction member of FIG. 4;

FIG. 8 is a fragmentary front plan view, partly broken away, of the hemostatic device of the present invention showing the catheter as positioned in the traction member;

FIG. 9 is a fragmentary sectional view taken substantially as indicated along the line 9—9 of FIG. 8;

FIG. 10 is a fragmentary front plan view of the hemostatic device illustrating use of the traction member to apply forces against the catheter shaft;

FIG. 13 is a fragmentary perspective view of another embodiment of an indicating element for the traction member of the present invention.

DESCRIPTION OF THE PREFERRED EMBODIMENTS

Figure 11:
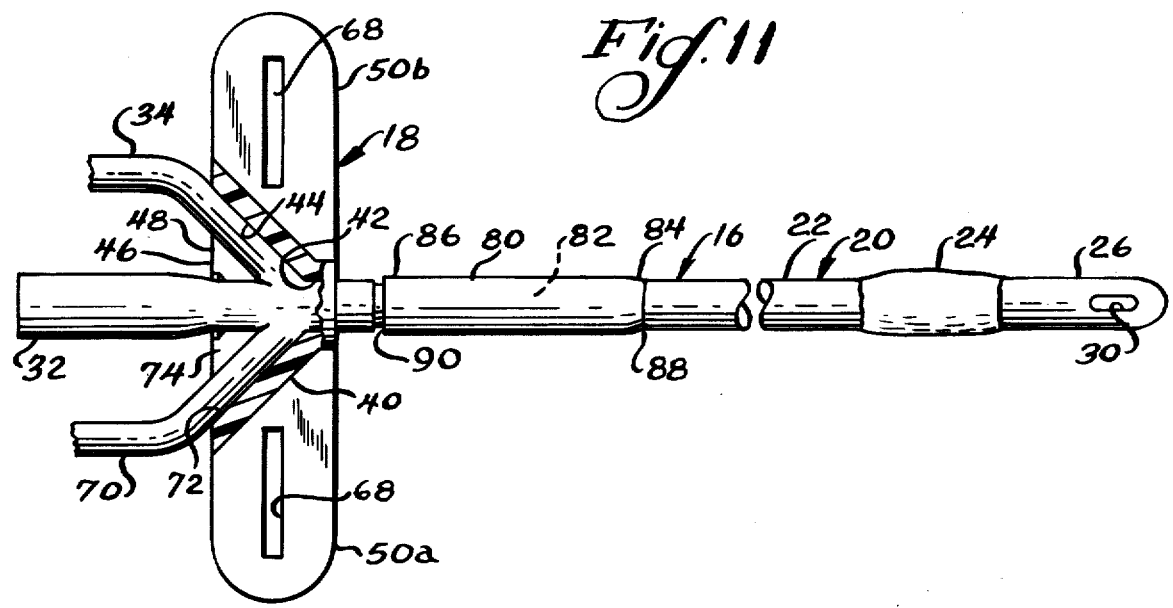
FIG. 11 is a fragmentary front plan view, partly broken away, of another embodiment of the hemostatic device of the present invention.

Referring now to FIGS. 8 and 9, there is shown a hemostatic device generally designated 16 having a traction member 18 and a catheter 20 removably received in the traction member 18. With reference to FIG. 3, the catheter 20 has an elongated shaft 22 of flexible and elastic material, such as latex rubber or silicone. The catheter 20 has an inflatable balloon 24 of flexible material secured to the shaft 22 adjacent a distal end 26 of the catheter 20, a drainage lumen 28 extending between one or more drainage eyes 30 adjacent the distal end 26 of the shaft 22 and a proximal end 32 of the catheter. The catheter 20 also has an inflation sidearm 34 adjacent the proximal end 32 of the catheter 20, with the sidearm 34 extending outwardly at an acute angle relative the shaft. The catheter has an inflation lumen 36 communicating between valve means (not shown) on the sidearm 34 and a cavity intermediate the balloon 24 and an outer surface of the shaft 22. The catheter shaft has a plurality of spaced lines or indicia 38 for a purpose which will be described below.

Referring to FIGS. 4-9, the traction member 18 has a retaining portion 40 having a bore 42 extending therethrough to receive the catheter shaft 22. The retaining portion 40 also has a side channel 44 communicating with the bore 42 and extending at an acute angle from the bore toward a proximal end 46 of the retaining portion 40. The retaining portion 40 also has a transverse slot 48 extending between the bore 42 and the side channel 44. In a preferred form, the inner dimensions of the bore 42 and side channel 44 are approximately equal to the respective outer dimensions of the catheter shaft 22 and sidearm 34, while the inner dimensions of the slot 48 are less than the dimensions of the catheter sidearm and shaft.

The traction member 18 has a pair of elongated attachment wings 50a and 50b extending from opposed sides of the retaining portion 40. As shown, the wings 50a and b may be relatively flat and define a generally planar attachment surface 52, with the surface 52 being generally aligned with a plane defined by the axes of the retaining portion bore 42 and side channel 44. As shown, the retaining portion may define a continuation of the attachment surface 52 intermediate the wings 50a and b. In a preferred form, the attachment surface 52 has an adhesive 54 covering the surface 52, and release sheets 56 releasably attached to and covering the adhesive 54.

The traction member 18 also has an indicating member 58 extending distally from the retaining portion 40. The indicating member 58 may comprise a generally tubular section 60 defining a continuation of the bore 42, and having an elongated opening 62 which is sufficiently large to permit passage of the catheter shaft through the opening 62. The indicating member 58 also defines a reference edge 64 at the distal end 66 of the traction member 18. The traction member 18 may be made of any suitable material, such as polyethylene or polyvinyl chloride.

With reference to FIG. 4, the distal end 26 of the catheter shaft 22 is inserted into the retaining portion bore 42, and the catheter shaft 22 is passed through the bore 42 until the catheter sidearm 34 is located adjacent the proximal end 46 of the traction member 18. Next, with reference to FIGS. 8 and 9, the catheter sidearm 34 is passed through the retaining portion slot 48 until the sidearm 34 is located in the retaining portion side channel 44. As shown, when the catheter 20 is placed in the traction member 18, the junction of the catheter shaft 22 and inflation sidearm 34 is located adjacent the juncture of the retaining portion bore 42 and side channel 44. In this configuration, the catheter 20 is firmly retained in the traction member 18, with the retaining portion 40 grippingly engaging against the catheter shaft 22 and sidearm 34. Also, in the relaxed condition of the catheter shaft, it will be seen that the reference markings or indicia 38 on the catheter shaft 22 are located beneath the indicating member 58 of the traction member 18.

With reference to FIG. 1, during prostatectomy the prostate P of a male patient is removed either suprapubically or by transurethral dissection, causing bleeding in the corresponding cavity or prostatic fossa C, illustrated in FIG. 2, defined by the removed prostate. In order to stop bleeding (hemostasis) in the prostatic fossa C, the hemostatic catheter 20 is passed through the patient's urethra U until the balloon 24 is located in the patient's bladder B where it is inflated, after which forces are applied against the proximal end of the catheter 20 which are transmitted through the catheter shaft 22 to the balloon 24. In turn, the inflated balloon 24 applies pressure against the apex of the incised blood vessels in the prostatic fossa C eventually causing hemostasis in the prostatic fossa C. During this time, it is desirable to know that the pressure applied by the balloon is sufficiently large to stop bleeding yet sufficiently small to minimize the possibility of pressure necrosis in the bladder which otherwise might be caused by excessive balloon pressure.

As shown in FIG. 10, the elastic catheter shaft 22 expands in a longitudinal direction responsive to the force applied against the catheter by the traction member, such that the shaft portion containing the indicia 38 increases in length relative the indicating member 58, thus exposing one or more of the indicia or reference markings 38 outside the reference edge 64 of the indicating member 58. In this manner, the amount of tension in the shaft may be determined by the number of reference markings 38 located outside the indicating member 58 after application of the force, with the reference markings 38 being appropriately calibrated in order that an accurate determination of the applied force and resulting pressure may be made. Thus, the traction member 18 and catheter shaft cooperate to measure an increase in length or expansion of the shaft portion beneath the indicating member 58 responsive to an increased tension in the catheter shaft 22. The urologist may utilize the hemostatic device of the present invention to determine the range of applied force desired to accomplish hemostatis after prostatectomy without causing pressure necrosis in the bladder. Once known, the urologist can establish the desired amount of applied force and balloon pressure through use of the reference markings 38 relative the reference edge 64 of the traction member 18.

After placement of the catheter in the patient, the release sheets 56 may be removed from the adhesive 54 on the traction member wings 50a and b, and the wings 50a and b may be attached to the patient's thigh with the catheter shaft in a stressed condition, and with the desired amount of tension being indicated by the indicating member 58 and reference markings 38. In this manner, the desired amount of pressure exerted by the catheter balloon 24 may be determined and maintained by the traction member to accomplish hemostasis through a period of time while minimizing the possibility of pressure necrosis. During this time, a drainage tube (not shown) may be attached to the proximal end 32 of the catheter 20 to permit drainage of urine through the catheter drainage eyes 30 and drainage lumen 28 into a collection bag (not shown) for retention therein. After hemostasis has been accomplished, the drainage tube may be removed from the catheter, and the traction member may be removed from the patient and from the catheter to permit continued drainage from the bladder, if desired.

Figure 12:
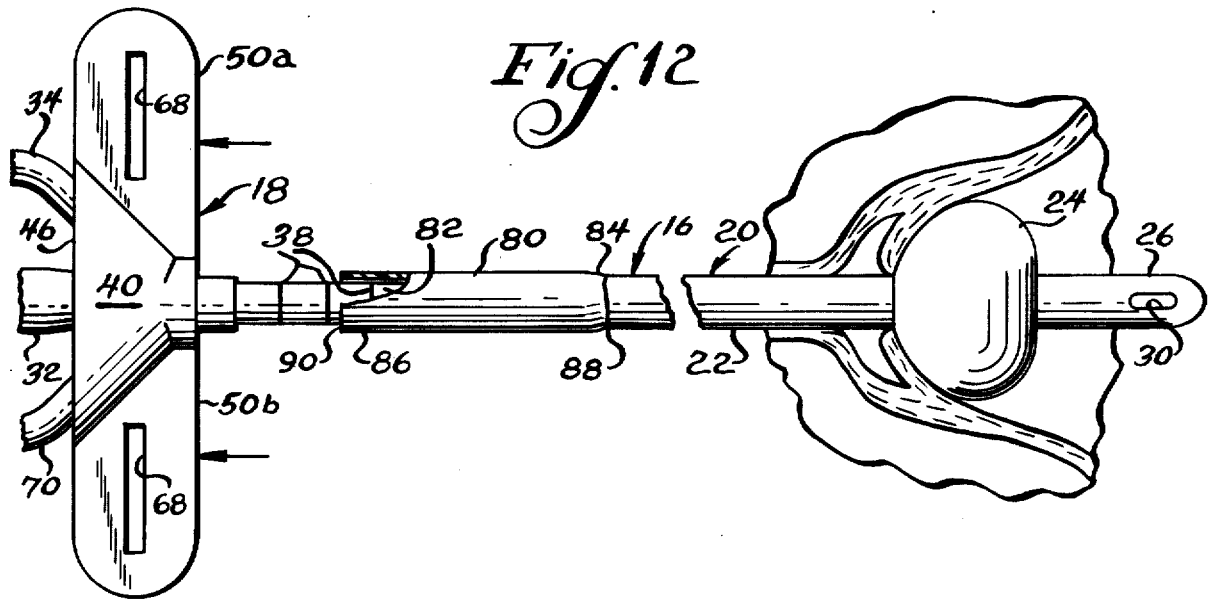
FIG. 12 is a fragmentary front plan view of the device of FIG. 11 during application of forces against the catheter shaft.

Another embodiment of the present invention is illustrated in FIGS. 11 and 12, in which like reference numerals designate like parts. In this embodiment, the wings 50a and b may have elongated slots 68 to permit passage of an attachment member, such as tape, through the slots in order to secure the wings to the patient or other object. In this embodiment, a catheter 20 having a second sidearm 70 is shown for use in irrigating the patient's bladder at periodic intervals. The second sidearm 70 extends outwardly from the catheter shaft 22 at an acute angle on a side opposed to the inflation sidearm 34. The retaining portion 40 of the traction member 18 has a second side channel 72 which communicates with the bore 42 and which extends at an angle from the bore on an opposed side of the bore relative the first side channel 44. The retaining portion 40 also has a second slot 74 extending between the bore 42 and the second side channel 72 to permit passage of the second sidearm 70 through the slot 74 into the second side channel 72 during placement of the catheter in the traction member 18. Thus, the catheter may be positioned in the traction member 18 in a manner as previously described in connection with the hemostatic device of FIGS. 1–10.

In this embodiment, the indicating member is omitted from the traction member, and, in lieu thereof, the catheter has a device for indicating the amount of tension in the catheter shaft. Thus, the catheter 20 has an elongated sleeve 80 overlying a longitudinal section 82 of the catheter shaft adjacent the traction member 18. The sleeve 80 has a first end portion 84 secured to the shaft 22 at a point 88, and a free second end portion 86 located proximal the first end portion 84, such that the sleeve 80 extends proximally from the first end portion 84 toward the traction member 18. The sleeve may be made from a flexible or relatively rigid material, as desired. In a preferred form, as shown, the sleeve 80 may comprise an integral extension of the catheter shaft 22 with the sleeve 80 being free of attachment from the catheter shaft 22 intermediate the connecting point 88 and a reference end edge 90 as defined by the second end portion 86 of the sleeve 80. The longitudinal section 82 of the catheter shaft 22 has a plurality of longitudinally spaced reference markings or indicia 38 located beneath the sleeve 80 in the normal relaxed configuration of the catheter 20.

Thus, the catheter shaft 22 expands in a longitudinal direction responsive to forces applied against the catheter, such that the longitudinal shaft section 82 increases in length relative the sleeve 80, thus exposing one or more of the indicia or reference markings 38 outside the reference edge 90 of the sleeve 80, as shown in FIG. 12. In this manner, the amount of tension in the shaft may be determined by the number of reference markings 38 located outside the sleeve 80 after application of the force, and the sleeve 80 and longitudinal section 82 cooperate to measure an increase in length or expansion of the longitudinal section 82 responsive to increased tension in the catheter shaft 22. Forces may thus be applied in the desired amount to the catheter shaft, and the traction member 18 may be secured to the patient's thigh in order to maintain the selected amount of tension in the catheter shaft and accomplish hemostasis, as previously described.

Another embodiment of the traction member 18 is illustrated in FIG. 13, in which like reference numerals designate like parts. In this embodiment, the indicating member 58 comprises a tubular section 60 having an elongated opening or window 92 extending through a wall of the indicating member 58. In this embodiment, the indicating member 58 may have a plurality of indicia or reference markings 38' spaced along the window 92 which cooperate with a reference marking on the catheter shaft to determine the desired amount of tension in the catheter shaft.

The foregoing detailed description is given for clearness of understanding only, and no unnecessary limitations should be understood therefrom, as modifications will be obvious to those skilled in the art.

I claim:

1. A hemostatic device, comprising:
   a catheter having an elongated shaft of elastic material, an inflatable balloon adjacent a distal end of the shaft, and a sidearm adjacent a proximal end of the catheter extending outwardly from the shaft;
   a traction member comprising, a retaining portion having a bore in which the catheter shaft is removably positioned, a side channel in which the catheter side arm is removably positioned communicating with said bore and extending at an angle from the bore toward a proximal end of the retaining portion, said retaining portion having a slot extending between the channel and bore to permit passage of the catheter sidearm into the side channel during placement of the catheter in the traction member with the juncture of the catheter shaft and sidearm being located adjacent the juncture of the retaining portion bore and side channel, said traction member having means for connecting the retaining portion to an object to maintain the catheter shaft under selected tension.

2. The device of claim 1 wherein the inner dimensions of said bore and side channel are approximately equal to the respective outer dimensions of the catheter shaft and sidearm.

3. The device of claim 1 wherein the inner dimensions of said slot are slightly less than the outer dimensions of the catheter sidearm.

4. The device of claim 1 wherein the connecting means comprises a pair of elongated wings extending outwardly from opposed sides of the retaining portion.

5. The device of claim 4 wherein said wings are relatively flat and define a plane generally aligned with a plane defined by the axes of said bore and side channel.

6. The device of claim 4 wherein said wings define an elongated generally planar attachment surface.

7. The device of claim 6 wherein said retaining portion defines a continuation of said attachment surface.

8. The device of claim 6 wherein said wings include an adhesive on said attachment surface, and release sheet means releasably attached to said adhesive.

9. The device of claim 4 wherein said wings include an elongated slot to permit passage of attachment members through said slots.

10. The device of claim 1 wherein said traction member includes an indicating element extending distally from said retaining portion to define a reference position relative the shaft.

11. The device of claim 10 wherein said indicating element extends at least partially circumferentially around the catheter shaft when the catheter is received in the traction member.

12. The device of claim 11 wherein said indicating element comprises a generally tubular section having an elongated opening sufficiently large to permit removal of the catheter shaft from the tubular section through said opening.

13. The device of claim 10 wherein said indicating element has a distal edge defining a reference position, and in which the catheter shaft has a plurality of spaced indicia alignable with the reference edge responsive to variable tension in the catheter shaft.

14. The device of claim 1 wherein said catheter has means for indicating the amount of tension in the catheter shaft.

15. The device of claim 1 wherein said catheter includes a second sidearm adjacent a proximal end of the shaft and extending outwardly from the shaft on a side opposed to the first sidearm, in which said retaining portion includes a second side channel communicating with said bore and extending at an angle from the bore on an opposed side of the bore relative the first side channel, and in which the retaining portion includes a slot extending between said bore and second side channel to permit passage of the second side arm into the second side channel during placement of the catheter in the traction member.

* * * * *